United States Patent [19]
Verfaillie

[11] Patent Number: 5,397,707
[45] Date of Patent: Mar. 14, 1995

[54] RECEPTACLE WITH POROUS WELDING THE USE AND THE MANUFACTURE THEREOF

[76] Inventor: Magda Verfaillie, Koning Boudewijnstraat 30, B-9820 Merelbeke, Belgium

[21] Appl. No.: 129,377

[22] Filed: Sep. 30, 1993

[51] Int. Cl.6 .............................................. C12M 1/04
[52] U.S. Cl. ................ 435/253.1; 435/252.1; 435/286; 435/818; 383/102; 383/107
[58] Field of Search ............... 383/100, 101, 102, 107; 435/243, 252.1, 253.1, 284, 286, 809, 818; 422/101, 102

[56] References Cited

U.S. PATENT DOCUMENTS 3,184,395 5/1965 Brewer ................................. 435/299
4,904,597 2/1990 Inoue et al. ....................... 435/252.1

*Primary Examiner*—David A. Redding
*Attorney, Agent, or Firm*—Sughrue, Mion, Zinn, Macpeak & Seas

[57] ABSTRACT

A receptacle made of one or several films, two parts of which are welded, the one with the other, by insertion of multifilament fibers so as to form a welding that stretches between two edges, thereby allowing the passage of gases therethrough but avoiding the passage of solid particles therethrough. Some fibers have a part stretching outside one edge of the weld, while other fibers have a part stretching outside the other edge of the weld. Also, a process for the incubation of mycelium growing medium.

12 Claims, 3 Drawing Sheets

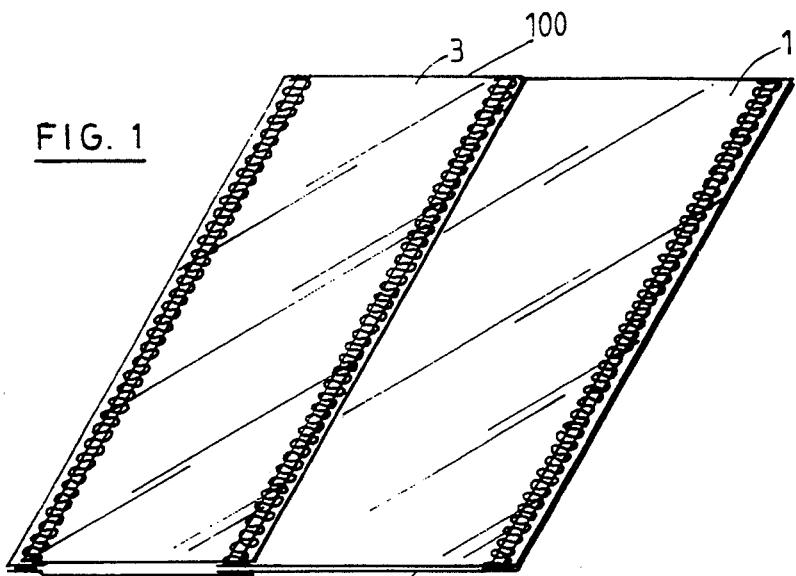
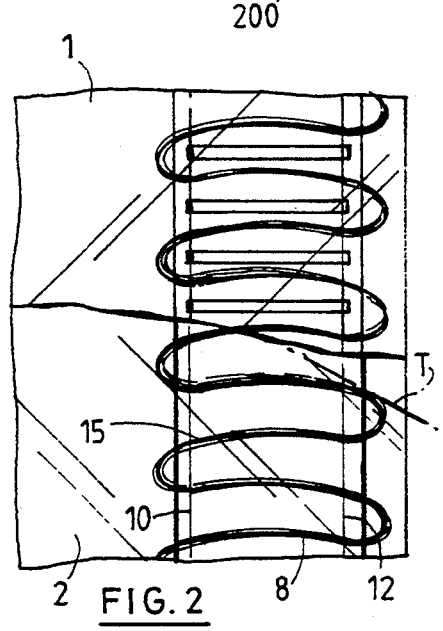
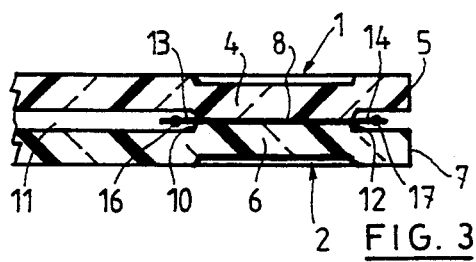
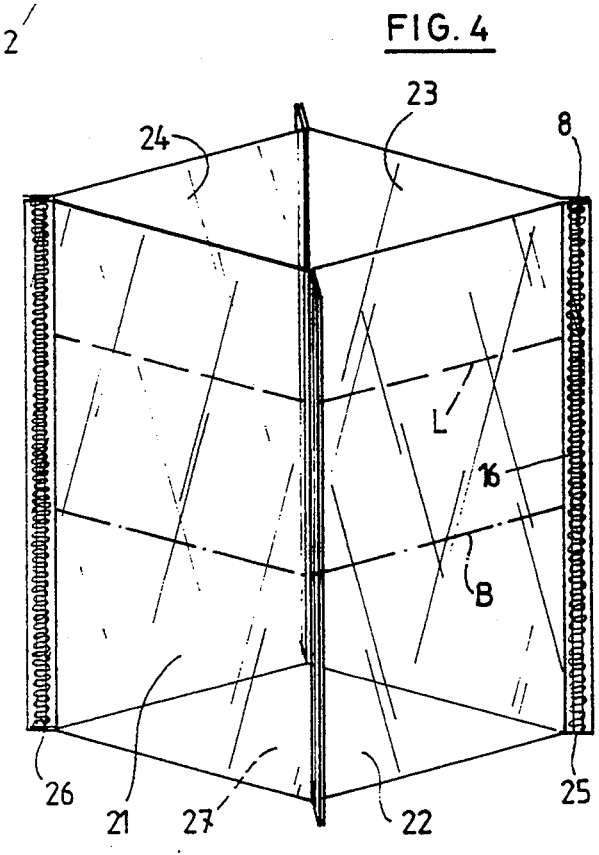

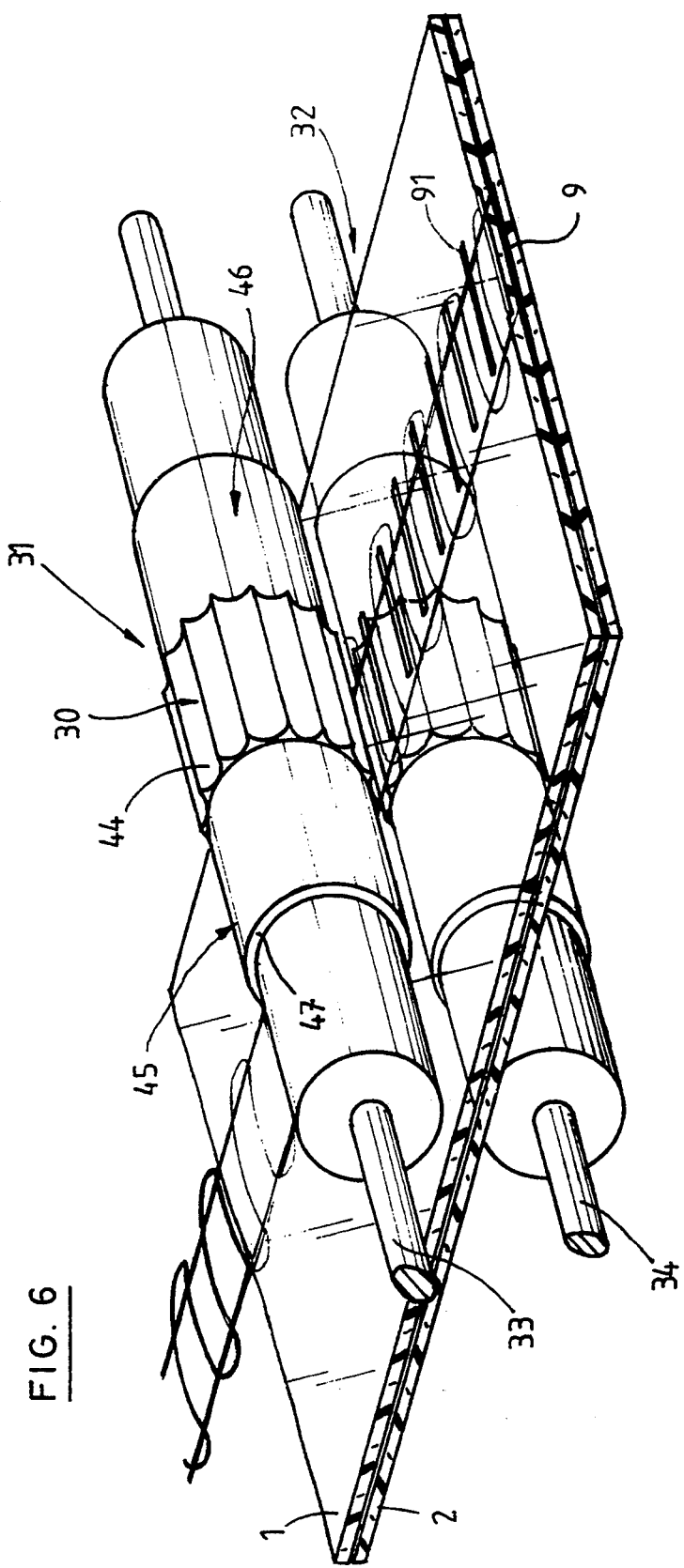

RECEPTACLE WITH POROUS WELDING THE USE AND THE MANUFACTURE THEREOF

THE STATE OF THE ART

The incubation of mycelium growing medium into a receptacle requires the passage of gases ($O_2$ towards the medium and evacuation of $CO_2$).

It has already been suggested to incubate mycelium growing medium into a bag, one side of which is made from a microporous sheet material or into a bag which is provided at its end with a closing means such as paper, cotton, wadding or microporous material.

Drawbacks of the bag with a side made from a microporous material are:
- no check of the growing can be effected on the microporous side as said side is opaque;
- higher dessication of the growing material in the neighbourhood of the microporous material;
- difficulty to ensure a well determined porosity as the thickness of the microporous sheet is low.

Drawbacks of the bag provided with a closing means are:
- high dessication rate of the growing material in the neighbourhood of the microporous material;
- low content of the bag.

Moreover, known bags have the drawback that the pores of the microporous material are obstructed by the growing mycelium in such a manner that substantially no gases exchange is still possible, whereby the grow of the mycelium growing material is low and not uniform.

The present invention has for subject matter a receptacle such as a bag, a sleeve, a container obviating the above mentioned drawbacks.

BRIEF DESCRIPTION OF THE INVENTION

The present invention relates to a receptacle such as a bag, sleeve, container made of one film or of several films, two parts of which are welded the one with the other with insertion of a means so as to form a welding stretching between two edges allo—the passage of gases therethrough said means comprising fibres, some fibres having a part stretching outside an edge of the welding, while some fibres have a part stretching outside the other edge of the welding.

Advantageously, the fibres, which may be continuous or multifilament fibres, are placed the one with respect to others so as to define channels in the welding, the narrow diameter or the diameter of the narrow passage thereof being lower to 1 $\mu$m.

Fibres may be all the same, i.e. same diameter, same composition but also different fibres can be used together, i.e. for example, one fibre may be made of a material suitable for making a welding while another fibre is not melted during the welding.

As the welding width can be made on a very precise manner as required, the channels or drains stretching into the welding have substantially the same length.

Moreover, as the channels or drains stretch into the welding, i.e. through its width, it can be ensured that the narrow diameter thereof is lower to 1 $\mu$m.

According to an embodiment, the fibres for forming channels in the welding are multifilament fibres, a channel formed by a part of the first multifilament fibre being adjacent to a channel formed by a part of a second multifilament fibre, said parts stretching between an inner end and an outer end, the inner and outer ends of the part of the first multifilament fibre which are located outside the welding being linked respectively to the inner and outer ends of the part of the second multifilament fibre. Advantageously, linking means links parts of multifilament fibres outside the welding.

According to be a specific embodiment, the fibres stretching in the welding from the inner edge to the outer edge are curved. According to a characteristic of said embodiment, the curve is such that the tangents of the curve at the inner and outer edges of the welding pass through at least one adjacent curve of adjacent fibres.

According to a preferred embodiment of the receptacle according to the invention, the fibres are placed the one with respect to others so as to define channels stretching between the two edges of the welding, the diameter of said channels being narrowed at a point located between the said two edges with respect to the diameter of said channels at said two edges.

Advantageously, the diameter of said channels is greater than 5 $\mu$m at the two edges of the welding while said diameter is lower to 1 $\mu$m at a point located between the two edges.

The invention relates also to a process for the incubation of mycelium growing medium in which:
- a growing medium is sterilized or pasteurized;
- said sterilized medium is placed, before or after sterilisation or pasteurisation, into a receptable made of at least one film, two parts of which are welded the one with the other with insertion of a means so as to form a welding stretching between two edges allowing the passage of gases therethrough, but avoiding the passage of solid particles therethrough, said means comprising fibres, some fibres having a part stretching outside an edge of the welding, while some fibres have a part stretching outside the other edge of the welding;
- the receptacle may be hermetically closed so that the passage of gases is only possible at the above mentioned welding and so that the passage of solid particles into the receptacle and out from the receptacle is not possible;
- the receptacle is placed into a preferably well ventilated room containing a substantially constant atmosphere;
- the growing medium contained in the receptacle placed in said room is maintained at a substantially constant temperature comprised between 20° and 30° C., and the maximum $CO_2$ level into the receptacle is kept in any part thereof lower to 3 volume %.

Another subject matter of the invention is a process for the manufacture of a receptacle made of at least one film in which two parts thereof are welded the one with the other with insertion of a means so as to form a welding stretching between two edges allowing the passage of gases therethrough, but avoiding the passage of solid particles therethrough, said means comprising fibres, some fibres having a part stretching outside an edge of the welding, while some fibres have a part stretching outside the other edge of the welding. Said welding is advantageously a high frequency welding.

Other particularities and details of the invention will appear from the following description in which reference is made to the attached drawings.

BRIEF DESCRIPTION OF THE DRAWINGS

FIG. 1 is a perspective view of a bag according to the invention;

FIG. 2 is a partial upper view, on an enlarged scale, of welded parts of the bag shown in FIG. 1;

FIG. 3 is a partial cross-section, on an enlarged scale, of a welded edge of the bag shown in FIG. 1;

FIG. 4 is a perspective view of a sleeve according to the invention;

FIG. 6 is a view on enlarged scale of a detail of the machine shown in FIG. 5.

DESCRIPTION OF THE INVENTION

Figure 5:
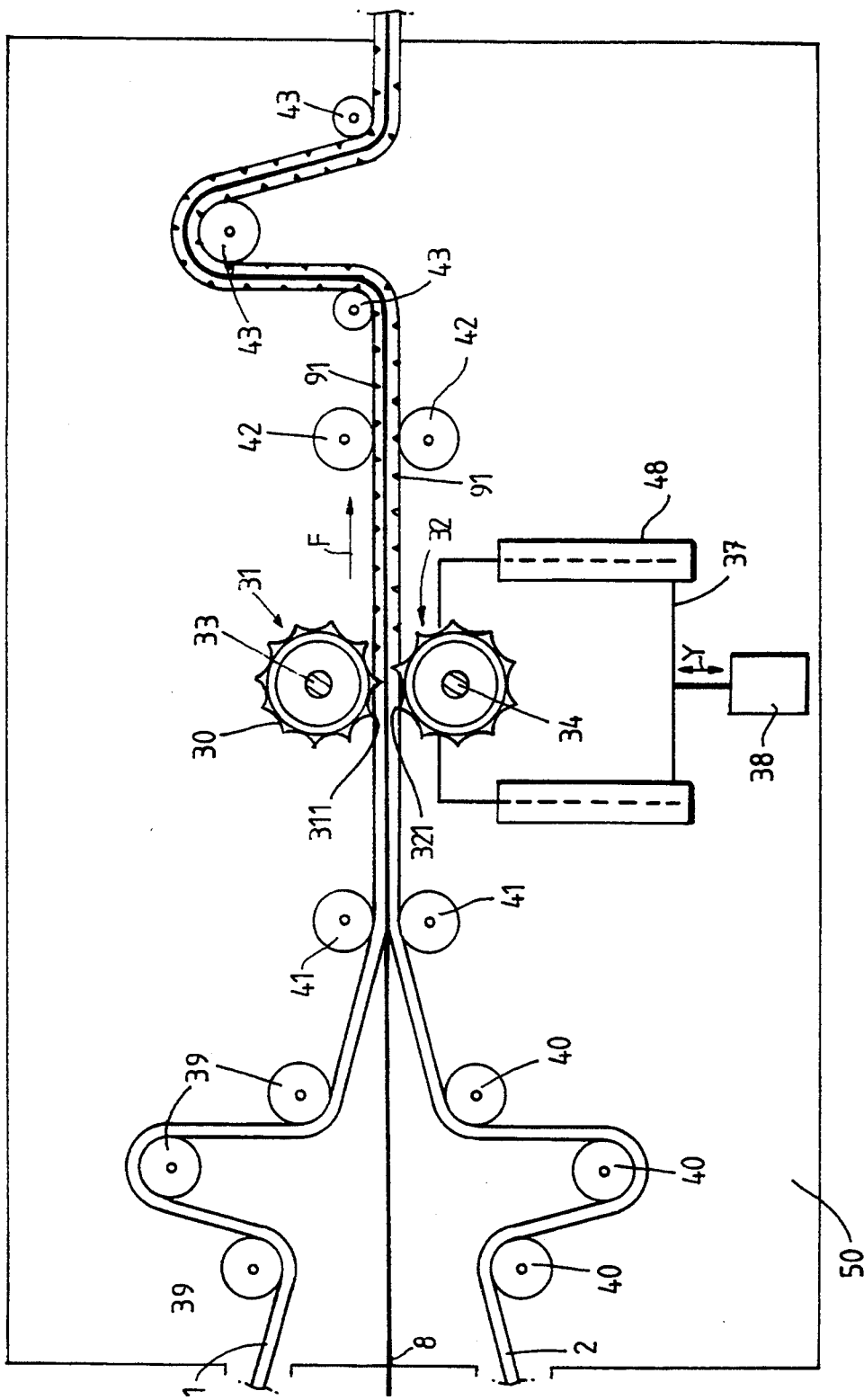
FIG. 5 is a shematic view of a part of a machine for the manufacture of a receptacle.

FIG. 1 shows a bag according to the invention. Said bag is comprised of several plastic (PVC, PE, PP) sheets 1,2,3 which are welded the one to another near their ends. For example, a part 4 near the end 5 of the sheet 1 is welded to part 6 adjacent to the end 7 of the sheet 2 with insertion of a means 8 comprising fibres. The bag can be closed at its edges 100, 200 by welding or every suitable means.

The means 8 stretches into the welding 9 which is situated between an inner edge 10 and an outer edge 12 with respect to the space 11 defined by the bag. The fibres have a part 13 stretching outside the inner edge 10 of the welding 9 and a part 14 stretching outside the outer edge 12 of the welding 9.

Channels 15 are formed between the multifilament fibres, said channels having a narrow part the diameter of which is lower than 1 $\mu$m, for example comprised between 0.5 and 0.8 $\mu$m. The diameter of said channels at the edges 10,12 of the welding is greater than 5 $\mu$m, for example comprised between 8 and 15 $\mu$m. Thus, the diameter of a channel varies from the inner edge 10 to the outer edge 12 of the welding 9. In the embodiment shown, the diameter is reduced from 10 $\mu$m at the inner edge 10 up to about 0.8 $\mu$m at a point P situated substantially at the middle of the welding 9 and is then increased from about 0.8 $\mu$m at point P to about 30 $\mu$m at the outer edge 12 of the welding 9.

Chains 16,17 link respectively parts 13 of the multifilament fibres located outside the inner edge 10 and parts 14 of multifilament fibres located outside the outer edge 12. Said chains form a protection for the channels and act as means so as to avoid the passage of big particles towards the edges of the welding 9.

The fibres 8 defining a channel 15 in the welding 9 are curved. Said curve is such that the tangents T of the curve at the inner edge and at the outer edge pass through an adjacent curve made from adjacent fibres (adjacent channel).

The channels 15 are indeed such that they allow the passage of gases ($O_2$, $CO_2$) through the welding, but avoid the passage of solid particles therethrough.

In the embodiment of FIG. 1, the upper surface and the lower surface are divided into surfaces having a width stretching between two weldings 9, of about 15 cm.

FIG. 4 shows a sleeve with a substantially sqare section.

The sleeve is comprised of fourth films 21,22,23,24, one film being welded to two films along its opposite longitudinal edges 25,26. Between the part of a first film and the part of another film welded to the part of said first film, a means 8 of the type shown in FIGS. 2 and 3 is inserted.

Such a sleeve is advantageously provided with a bottom 27 so that a container is formed, container suitable for containing a medium on which the growth of a plant or any living organisms is ensured. The medium fills for example the sleeve up to a level L, while the container is placed into a liquid or substantially liquid bath, the upper level of which B is lower to the level L.

The means 8 is then such as to allow nutrituve molecules to flow from the bath into the medium. In said case, chain 16 acts as a diffusion means so as to ensure a random distribution of the nutritive element or molecule into the medium, i.e. so as to ensure a substantially uniform growth of the root whatever be the direction thereof.

A bag as shown in FIG. 1 is suitable for the incubation of mycelium growing medium. For example, the process for incubating mycelium growing medium comprises the following steps:

A growing medium is sterilized or pasteurised;

The sterilized medium is placed into the bag;

the bag is closed so that only passage of gases is possible through the channels of the welding;

the bag is placed in a room, the temperature and humidity of which are controlled so that its atmosphere remains substantially constant. The growing medium in the bag is therefore maintained at a substantially constant temperature, for example of 25° C. By means of the channels, preferably located at least along two opposite edges of the bag, and as the channels remain open for the passage of gases particles lower to 1 $\mu$m, the maximum $CO_2$ level into the bag can be maintained at every place lower to 3% volume.

Possibly the sterilisation or pasteurisation can be made after placing the growing material into the bag.

Bag according to the invention can be manufactured by means of a welding machine.

Said welding machine comprises a high frequency or ultrasonic welding head 30 and a means for pressing the one to the other the two parts to be welded together. Said pressing means is comprised of an upper toothed wheel or roller 31 and a lower toothed wheel or roller 32. All said means or elements are attached to a frame 50.

A tooth 321 of wheel 32 is engaged into the recess located between two teeth 311 of wheel 31. Wheel 31 is mounted on a shaft 33, while wheel 32 is secured on a shaft 34 driven by a motor (not shown). Said shaft 34 is driven into rotation so that a tooth 321 pushes at least one part to be welded in a direction corresponding to the forward movement F of the welded part. A brake can possibly act on shaft 33 so as to ensure a high pressing of the parts to be welded between a tooth of the upper wheel and a tooth of the lower wheel.

By means of said machine a very good welding 9 can be obtained, said welding appearing as being formed by adjacent parallel welding lines 91.

Moreover the channels are by means of said machine distributed on a uniform manner along the welding and have substantially constant properties, such as length, narrow diameter, curve, . . . .

So as to press the parts to be welded, a means acts avantageously so as to push one wheel or roller towards the other wheel or roller. For example, the roller 32 is mounted on a shaft 34 fixed on a plate 37 able to slide along rails 48 towards the roller 31. The sliding (Arrow Y) of the roller 32 towards the roller 31 is effected by means of a jack 38 acting on the plate 37. Said jack (or a spring according to another embodiment) acts as a means for ensuring a minimum or substantially constant pressure between the two parts to be welded.

The films to be welded are uncoiled and pass through rollers 39,40 which are driven into rotation by motors (not shown) so as to ensure a stretching of the films before the welding.

The films pass also before and after the welding between rollers 41,42 so as to ensure the films are correctly placed for the welding.

After the welding, the welded films are kept in a stretch status by means of driven rollers 43 between which the films pass.

In the embodiment of the used machine, the rollers 31, 32 are comprised of a central toothed part 44 and of two untoothed adjacent parts 45, 46 provided with a resilient layer 47 (such as a rubber layer).

By using such rollers, the films are also pressed near the welding during said welding, this ensuring still a better welding.

In the embodiments shown, the channels are obtained by using a plurality of fibres (for example more than 30 or preferably 50) having a diameter lower to 200 μm (preferably 75 μm). Such fibres are, for example, polyester fibres with a 280 to 1100 decitex.

What I claim is:

1. Process for the incubation of mycelium growing medium in which:
   a growing medium is sterilized;
   said sterilized medium is placed into a bag made of one film;
   the bag is closed;
   the bag is placed into a room containing a substantially constant atmosphere;
   the growing medium contained in the bag placed in said room is maintained at a substantially constant temperature comprised between 20° and 30° C.; the improvement consisting of the fact that a first part of the film is welded with a second part of the film with insertion of multifilament fibres, said multifilament fibres extending through the welding from an inner edge of the welding, said inner edge being directed towards the inner space defined by the bag, to an outer edge of the welding, said outer edge being directed towards the space outside the bag, as well as partly outside the welding, so as to form channels through the welding, said channels allowing the passage of gases therethrough while avoiding the passage of solid particles, so that,
   the maximum $CO_2$ level into the bag is kept in any place thereof at a level lower to 3 volume %.

2. Process for the incubation of mycelium growing medium, in which
   a growing medium is placed into a bag made of one film;
   the bag is closed;
   the growing medium in the bag is sterilized;
   the bag is placed into a room containing a substantially constant atmosphere;
   the growing medium contained in the bag placed in said room is maintained at a substantially constant temperature comprised between 20° and 30° C.,
   the improvement consisting of the fact that a first part of the film is welded with a second part of the film with insertion of multifilament fibres, said multifilament fibres extending through the welding from an inner edge of the welding, said inner edge being directed towards the inner space defined by the bag, to an outer edge of the welding, said outer edge being directed towards the space outside of the bag, as well as partly outside the welding, so as to form channels through the welding, said channels allowing the passage of gases therethrough while avoiding the passage of solid particles, so that,
   the maximum $CO_2$ level into the bag is kept in any place thereof at a level lower to 3%.

3. The process of claim 1, in which the multifilament fibres define channels through the welding, the narrow diameter of the channels being lower to 1μ.

4. The process of claim 11, in which the channels extending through the welding have substantially the same length.

5. The process of claim 2, in which the multifilament fibres define channels through the welding, the narrow diameter of the channels being lower to 1μ.

6. The process of claim 2, in which the channels extending through the welding have substantially the same length.

7. Process for the incubation of mycelium growing medium, in which
   a growing medium is sterilized;
   said sterilized medium is placed into a bag made of films welded together;
   the bag is closed;
   the bag is placed into a room containing a substantially constant atmosphere;
   the growing medium contained in the bag placed in said room is maintained at a substantially constant temperature comprised between 20° and 30° C.;
   the improvement consisting of the fact that a first part of a film is welded to a second part of another film with insertion of multifilament fibres, said multifilament fibres extending through the welding from an inner edge of the welding, said inner edge being directed towards the inner space defined by the bag, to an outer edge of the welding, said outer edge being directed towards the space outside of the bag, as well as partly outside the welding, so as to form channels through the welding, said channels allowing the passage of gases therethrough while avoiding the passage of solid particles, so that the maximum $CO_2$ level into the bag is kept in any place thereof at a level lower to 3 volume %.

8. The process of claim 7, in which the multifilament fibres define channels through the welding, the narrow diameter of the channels being lower to 1μ.

9. The process of claim 7, in which the channels extending through the welding have substantially the same length.

10. Process for the incubation of mycelium growing medium, in which
    a growing medium is placed into a bag made of films welded together;
    the bag is closed;
    the growing medium in the bag is sterilized;
    the bag is placed into a room containing a substantially constant atmosphere;
    the growing medium contained in the bag placed in said room is maintained at a substantially constant temperature comprised between 20° and 30° C.;
    the improvement consisting of the fact that a first part of a film is welded to a second part of another film with insertion of multifilament fibres, said multifilament fibres extending through the welding from an inner edge of the welding, said inner edge being directed towards the inner space defined by the bag, to an outer edge of the welding, said outer edge being directed towards the space outside the bag, as well as partly outside the welding, so as to form channels through the welding, said channels allowing the passage of gases therethrough while avoiding the passage of solid particles, so that the maximum $CO_2$ level into the bag is kept in any place thereof at a level lower to 3 volume %.

11. The process of claim 10, in which the multifilament fibres define channels through the welding, the narrow diameter of the channels being lower to $1\mu$.

12. The process of claim 10, in which the channels extending through the welding have substantially the same length.

* * * * *